(12) United States Patent
Iwamoto (10) Patent No.: US 8,758,586 B2
(45) Date of Patent: Jun. 24, 2014

(54) REFERENCE ELECTRODE (75) Inventor: Yasukazu Iwamoto, Kyoto (JP)

(73) Assignee: Horiba, Ltd. (JP)

( * ) Notice: Subject to any disclaimer, the term of this patent is extended or adjusted under 35 U.S.C. 154(b) by 243 days.

(21) Appl. No.: 13/325,193

(22) Filed: Dec. 14, 2011

(65) Prior Publication Data

US 2012/0152741 A1  Jun. 21, 2012

(30) Foreign Application Priority Data

Dec. 17, 2010  (JP) .................. 2010-282281

(51) Int. Cl.
G01N 27/30 (2006.01)
(52) U.S. Cl.
USPC ........................................ 204/435
(58) Field of Classification Search
USPC ........................................ 204/435
See application file for complete search history.

(56) References Cited

U.S. PATENT DOCUMENTS 3,681,136 A * 8/1972 Leonard et al. ............ 427/126.1

FOREIGN PATENT DOCUMENTS

| EP | 0247535 | A2 | * | 5/1987 |
| EP | 0433261 | A1 | | 6/1991 |
| GB | 2093193 | A | | 8/1982 |
| GB | 2469650 | A | * | 10/2010 |
| JP | 5-340914 | A | | 12/1993 |
| JP | 4054246 | B2 | | 12/2007 |

OTHER PUBLICATIONS

EPO computer-generated translation of the Description section of Russell et al. EP 0247535 A2, patent published May 22, 1987.*
EPO computer-generated translation of the Claims section of Russell et al. EP 0247535 A2, patetn published May 22, 1987.*
Partial European Search Report for Application No./Patent No. 11193385.9-2204, dated Apr. 26, 2012.
Iida Y et al.: "Electrochemical enhancement for flow-amperometric biosensing with an oxidase column", Sensors and Actuators B: Chemical: International Journal Devoted to Research and Development of Physical and Chemical Transducers, Elsevier S.A., Switzerland, vol. 91, No. 1-3, Jun. 1, 2003, pp. 175-179.
Extended European Search Report for Application No./Patent No. 111933859-2204/2466296, dated Jul. 30, 2012.
P.J. Kinlen et al. "A solid-state pH sensor based on a Nafion-coated iridium oxide indicator electrode and a polymer-based silver chloride reference electrode", Sensors and Actuators B: Chemical: International Journal Devoted to Research and Development of Physical and Chemical Transducers, Elsevier S.A., Switzerland, vol. 22, No. 1, Oct. 1, 1994, pp. 13-25.
F. Kobayashi et al. "Stability of UNCl in LiCl-KCl eutectic melt", Journal of Alloys and Compounds, Elsevier Sequoia, Lausanne, Ch, vol. 271-273, Jun. 12, 1998, pp. 374-377.

(Continued)

Primary Examiner — Alex Noguerola
(74) Attorney, Agent, or Firm — Cantor Colburn LLP (57) ABSTRACT The present invention is intended to enable silver ions in an internal electrolyte solution of a reference electrode to be suppressed from being eluted, and also suppress a potential variation that occurs due to production of a poorly-soluble silver compound on surfaces of a liquid communication part and the like, and specifically provided with: an internal electrode formed of a silver/silver chlorides electrode; an internal electrolyte solution that is in contact with the internal electrode; and a containing body that contains the internal electrolyte solution, in which the containing body is formed of a material that does not have anionic conductivity but has cationic conductivity and moisture permeability.

3 Claims, 10 Drawing Sheets (56) References Cited

OTHER PUBLICATIONS

T. Murakami et al. "Electrochemical formation of uranium-zirconium alloy in LiCl-KCl melts", Journal of Nuclear Materials, Elsevier BV, NL, vol. 394, No. 2-3, Nov. 1, 2009, pp. 131-135.

A. Simonis et al. "Miniaturised reference electrodes for field-effect sensors compatible to silicon chip technology", Electrochimica ACTA, Elsevier Science Publishers, Barking GB, vol. 51, No. 5, Nov. 10, 2005, pp. 930-937.

* cited by examiner

Reference potential and resistances of reference electrode (initial values)

| No | Potential (mV) | Resistance (Ω) |
|---|---|---|
| 1 | -1.7 | 150 |
| 2 | -1.6 | 140 |
| 3 | -1.5 | 120 |
| 4 | -1.6 | 180 |
| 5 | -1.8 | 180 |
| 6 | -2 | 180 |
| 7 | -1.6 | 230 |
| 8 | -1.5 | 170 |
| 9 | -1.5 | 350 |
| 10 | -1.7 | 220 |
| 11 | -1.5 | 210 |
| 12 | -1.8 | 600 |
| 13 | -1.8 | 260 |
| Mean value | -1.662 | 230 |
| Standard deviation | 0.156 | 125.963 |
| CV value | -0.094 | 0.548 |

Reference potential and resistances of reference electrode (after one month)

| No | Potential (mV) | Resistance (Ω) |
|---|---|---|
| 1 | -1.6 | 130 |
| 2 | -1.6 | 140 |
| 3 | -1.5 | 100 |
| 4 | -1.6 | 150 |
| 5 | -1.6 | 160 |
| 6 | -1.8 | 170 |
| 7 | -1.5 | 180 |
| 8 | -1.6 | 150 |
| 9 | -1.6 | 180 |
| 10 | -1.6 | 150 |
| 11 | -1.7 | 210 |
| 12 | -1.3 | 160 |
| 13 | -1.5 | 150 |
| Mean value | -1.577 | 156.1538462 |
| Standard deviation | 0.117 | 26.627 |
| CV value | -0.074 | 0.171 |

Fig.4

| No | Reference electrode potential (mV) | | |
|---|---|---|---|
| | in #300 | sat. KCl | 0.001 Mol/L KCl |
| 1 | −1.6 | 4.1 | −130.0 |
| 3 | −1.4 | 5.0 | −129.6 |
| 12 | −1.0 | 4.6 | −131.2 |
| 1 | −2.0 | −10.5 | 132.6 |
| 3 | −2.2 | −10.6 | 134.2 |
| 5 | −2.5 | −10.9 | 132.0 |

Comparison electrode of the present embodiment (rows 1, 3, 12)

Conventional comparison electrode (rows 1, 3, 5)

(#300: 3.33mol/L KCl solution)

Fig.5

| No | Reference electrode potential (mV) | | |
|---|---|---|---|
| | in #300 | 0.1M KI added | |
| 1 | −1.5 | −0.6 | ⎫ Comparison electrode of |
| 3 | −1.5 | −0.3 | ⎬ the present embodiment |
| 12 | −1.2 | −0.5 | ⎭ |
| 3 | −2.4 | −32.4 | ⎫ Conventional comparison |
| 5 | −2.3 | −32.0 | ⎬ electrode |
| 12 | −2.3 | −34.0 | ⎭ |

(#300: 3.33mol/L KCl solution)

Fig.6

| No | Comparison electrode potential (mV) | | Potential difference (mV) |
|---|---|---|---|
| | in #300 (shielded in dark box) | in #300 (under direct sunlight) | |
| 1 | -1.2 | -1.3 | -0.1 |
| 2 | -0.5 | -0.5 | 0.0 |
| 3 | -0.3 | -0.4 | -0.1 |
| 4 | -0.5 | -0.5 | 0.0 |
| 5 | -1.0 | -1.0 | 0.0 |
| 6 | -0.3 | -0.5 | -0.2 |
| 7 | -1.0 | -1.2 | -0.2 |
| 8 | -0.5 | -0.5 | 0.0 |
| 9 | -1.0 | -0.9 | 0.1 |
| 10 | -0.4 | -0.4 | 0.0 |
| 11 | -0.5 | -0.6 | -0.1 |
| 12 | -1.0 | -1.2 | -0.2 |
| 13 | -1.1 | -1.2 | -0.1 |

(#300:3.33mol/L KCl solution)

Before drying

| No | Potential (mV) | Resistance (Ω) |
|---|---|---|
| 4 | -1.5 | 150 |
| 5 | -1.4 | 160 |
| 6 | -1.5 | 170 |

⇩

After immersion for 1day in 3.33 mol/L KCl solution

| No | Potential (mV) | Resistance (Ω) |
|---|---|---|
| 4 | -1.7 | 100 |
| 5 | -1.6 | 160 |
| 6 | -1.5 | 160 |

REFERENCE ELECTRODE

TECHNICAL FIELD

The present invention relates to a reference electrode in which an internal electrode made of silver/silver chloride electrolyte is provided in internal liquid.

BACKGROUND ART

As a conventional reference electrode, as disclosed in Patent literature 1, there is one that is provided with: an internal electrode formed of a silver/silver chloride electrode; a highly concentrated (1 mol/L or more, including saturation) internal electrolyte solution such as KCl that is in contact with the internal electrode; and a containing body that contains the internal electrolyte solution and has a liquid communication part for bringing the internal electrolyte solution into contact with a sample solution.

However, the conventional reference electrode has a problem that silver ions are eluted from the silver/silver chloride electrode, and by reaction with highly concentrated Cl⁻ ions in the internal liquid, anionic silver complex ions such as silver chloride complexation anions (such as $AgCl_2^-$) are produced, and when in the liquid communication part, the silver chloride complexation anions come into contact with the solution having a low chloride ion concentration, at an interface in contact with liquid, silver chloride (AgCl) is reprecipitated to block the liquid communication part, which causes electrode performance to be reduced.

In recent years, in order to solve the above problem, as disclosed in Patent literature 2, an electrode that is, in an internal electrolyte solution, provided with a silver ion adsorbing material that adsorbs silver ions is considered. The electrode is configured such that by adsorbing the silver ions that are eluted on the silver ion adsorbing material, a liquid communication part is not clogged by silver chloride.

However, in a reference electrode having a silver ion trap structure such as the silver ion adsorbing material provided in the internal electrolyte solution as described above, the structure not only complicates a configuration of the reference electrode but becomes a factor for causing the reference electrode to be enlarged or preventing the reference electrode from being downsized. Also, the reference electrode having the silver ion trap structure as described has a problem because the reference electrode is invented from the perspective of preventing the silver ions eluted from a silver/silver chloride electrode from flowing outside, and when efficacy of the silver ion trap structure is reduced, the liquid communication part is clogged by silver chloride after all unless the internal electrolyte solution is regularly replaced, which necessitates the replacement of the reference electrode itself.

CITATION LIST

Patent Literature

Patent literature 1: JPA Heisei 05-340914
Patent literature 2: Japanese patent No. 4054246

SUMMARY OF INVENTION

Technical Problem

Therefore, the present invention is made to solve the above problems at once, and has a main desired object to provide a reference electrode that prevents silver ions from being eluted from a silver/silver chloride electrode as well as preventing silver chloride from being precipitated on a surface of the reference electrode to thereby stabilize a reference electrode potential for a long time, and even if an internal solution of the reference electrode is decreased in volume due to drying, shortens a recovery time of the potential.

Solution To Problem

That is, a reference electrode according to the present invention is provided with: an internal electrode formed of a silver/silver chloride electrode: an internal electrolyte solution that is in contact with the internal electrode; and a containing body that contains the internal electrolyte solution, wherein the containing body is formed of a material that does not have anionic conductivity but has cationic conductivity and moisture permeability.

Note that "the containing body is formed of a material that does not have anionic conductivity but has cationic conductivity and moisture permeability" refers to a concept including: (a) a part of the containing body is made of the material and the other part is made of a material that does not have anionic conductivity, cationic conductivity, or moisture permeability; (b) a whole of the containing body is formed of the material that does not have anionic conductivity but has cationic conductivity and moisture permeability; and (c) the containing body has moisture permeability as a whole, a part of the containing body does not have anionic conductivity but has cationic conductivity, and the other part is made of a material that has anionic conductivity and cationic conductivity and does not have any hole.

If so, the containing body does not have anionic conductivity, and therefore chloride ions and anionic silver complex ions such as silver chloride complexation anions produced by reaction with the chloride ions and silver ions eluted from the silver/silver chloride electrode can be suppressed from being eluted. This enables silver ions in the internal electrolyte solution of the reference electrode to be suppressed from being eluted, and also a potential variation occurring due to production of a poorly-soluble silver compound on surfaces of a liquid communication part and the like to be suppressed.

Note that the anionic silver complex ions such as the silver chloride complexation anions do not flow out of the containing body, but are saturated in the internal electrolyte solution. Accordingly, a dissolution reaction of the silver chloride complexation anions (anionic silver complex ions) into the internal electrolyte solution is equilibrated. For this reason, it is considered that silver ions eluted from silver chloride are kept at a low concentration and do not diffuse into the internal electrolyte solution. This enables a silver/silver chloride electrode having a relatively thin silver chloride layer to be employed, or a life of the silver/silver chloride electrode to be extended.

More specifically, a chemical reaction inside the containing body $AgCl+Cl^- \rightarrow AgCl_2^-$ proceeds in the right direction because of anionic complex formation. However, the containing body prevents anions from passing therethrough, and therefore the above reaction is equilibrated soon.

That is, the reaction $AgCl+Cl^- \leftrightarrows AgCl_2^-$ is equilibrated, and silver ions eluted from silver chloride will have a concentration depending on a solubility product ($Ag^+$ ion concentration around $10^{-5}$ mol/L is kept).

Also, according to the present invention, the containing body does not have anionic conductivity but has cationic conductivity, so that the containing body prevents sulfide, iodide, or bromide ions influencing an electrode potential from passing therethrough, and therefore does not receive the coexistence influence of these anions. A potential difference generated between the inside and outside of the containing body depends on a cation concentration of the internal electrolyte solution. On the basis of this, a measurement error due to blockage of a liquid communication part caused by a precipitation reaction with chloride such as potassium chloride in the internal electrolyte solution can be eliminated. In the case where the internal electrolyte solution is, for example, a highly concentrated (e.g., 3.3 mol/L) KCl or $KNO_3$ solution, the reference electrode is typically immersed in a highly concentrated (e.g., 3.3 mol/L) KCl solution, so that a $K^+$ ion concentration (activity) is the same between the inside and outside of the containing body, and therefore a potential generated in the containing body is zero. In the case of using potassium nitrate as the internal liquid, a sample that gives rise to the above precipitation reaction with chloride or other reaction can be measured.

Further, according to the present invention, the containing body is formed of a material having moisture permeability, and therefore even if the internal electrolyte solution of the containing body is decreased in volume due to evaporation, only by immersing the reference electrode in a desired electrolyte solution, water can be made to permeate the containing body by vapor pressure balance. Based on this, only by immersing the reference electrode in a desired electrolyte solution, the internal electrolyte solution can be recovered to an original state, and also a reference potential can be recovered in a short time. Further, the containing body is only required to be immersed in a desired electrolyte solution, and therefore recovery work can be easily performed in a short time.

In addition, the containing body is only required to be formed of the material that does not have anionic conductivity but has cationic conductivity and moisture permeability, and therefore production cost can be reduced on the basis of saving of an assembling man-hour.

In order to make the effects of the present invention further remarkable, a whole of the containing body is preferably formed of a material that does not have anionic conductivity but has cationic conductivity and moisture permeability.

As a specific embodiment for making it possible to save an assembling man-hour and reduce production cost, the containing body is preferably a bottom-equipped tubular body formed of a material that does not have anionic conductivity but has cationic conductivity and moisture permeability.

Also, a reference electrode according to the present invention has: an electrode main body comprising silver; an eutectic salt layer covering the electrode main body, the eutectic salt layer comprises an eutectic mixture of silver chloride and a salt and the eutectic layer acts as an electrolyte; and an outside covering layer comprising a material having cationic conductivity and moisture permeability, and the outside covering layers covers the eutectic salt layer.

It is known that an electrode potential of the silver/silver chloride electrode is largely influenced by ultraviolet light (maximum absorption wavelength 220 nm), and in order to reduce the influence of ultraviolet light on the silver/silver chloride electrode, silver sulfide is preferably contained in the silver chloride eutectic salt. If so, silver sulfide absorbs ultraviolet light, and therefore the influence of ultraviolet light on the silver/silver chloride electrode can be reduced.

Advantageous Effects of Invention

According to the present invention configured as described, there can be provided a reference electrode that can prevent silver ions from being eluted from a silver/silver chloride electrode as well as preventing silver chloride from being precipitated on a surface of the reference electrode to thereby stabilize a reference electrode potential for a long time, and even if an internal solution of the reference electrode is decreased in volume due to drying, shorten a recovery time of the potential.

DESCRIPTION OF EMBODIMENTS

In the following, one embodiment of a composite electrode having a reference electrode (hereinafter also referred to as a comparison electrode) according to the present invention is described referring to the drawings.

Figure 1:
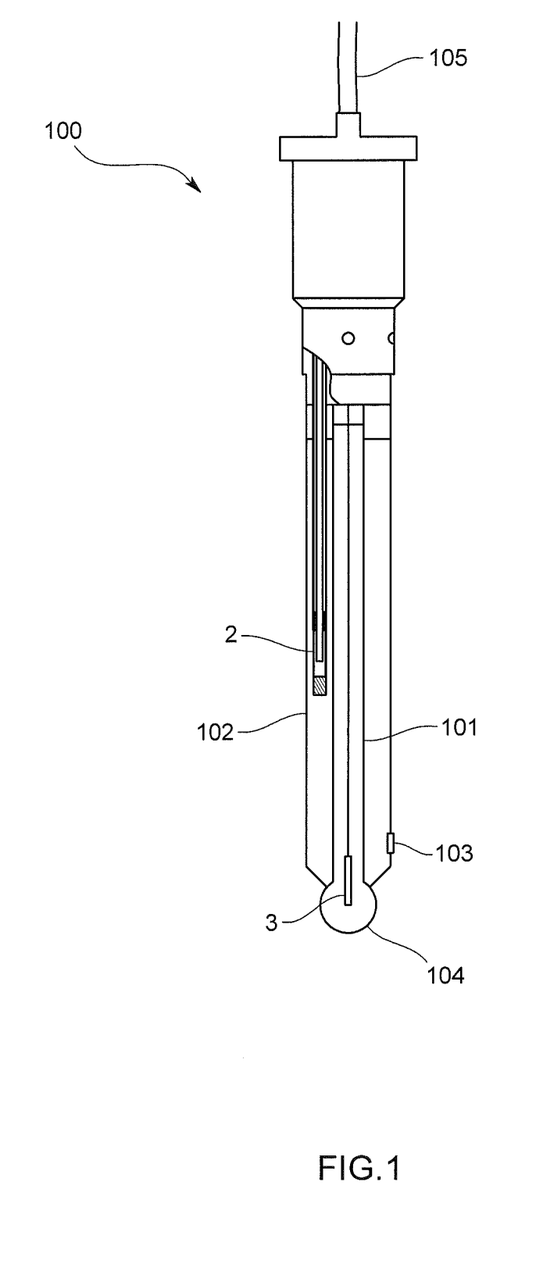
FIG. 1 is an overall schematic diagram schematically illustrating a configuration of a composite electrode of the present embodiment.

A comparison electrode 2 according to the present embodiment constitutes a composite electrode 100 integrally with a pH electrode 3 as illustrated in FIG. 1. Also, the composite electrode 100 is configured such that at least a cylindrical pH electrode supporting tube 101 and a comparison electrode supporting tube 102 surrounding an outer circumference of the pH electrode supporting tube 101 are integrally provided. Note that the pH electrode supporting tube 101 and the comparison electrode supporting tube 102 are both formed of glass having the same composition.

An outer circumferential wall of the comparison electrode supporting tube 102 is provided with a liquid communication part 103, and at a fore end portion of the pH electrode supporting tube 101 of which the fore end portion is projected slightly further than the comparison electrode supporting tube 102, a responsive glass membrane 104 is joined.

In the comparison electrode supporting tube 102 and the pH electrode supporting tube 101, the comparison electrode 2 and the pH electrode 3 are respectively contained, and as internal liquid, for example, a highly concentrated (3.33 mol/L) KCl solution with a pH of 7 is filled. Note that as the internal liquid for the comparison electrode supporting tube 102, for example, potassium nitrate having a concentration of 1.0 mol/L may be used. The comparison electrode 2 and the pH electrode 3 are respectively connected with unillustrated leads, and the leads extends outside from a base part of the pH electrode supporting tube 101 as a cable bundle 105 and is connected to an unillustrated pH meter main body.

Figure 2:
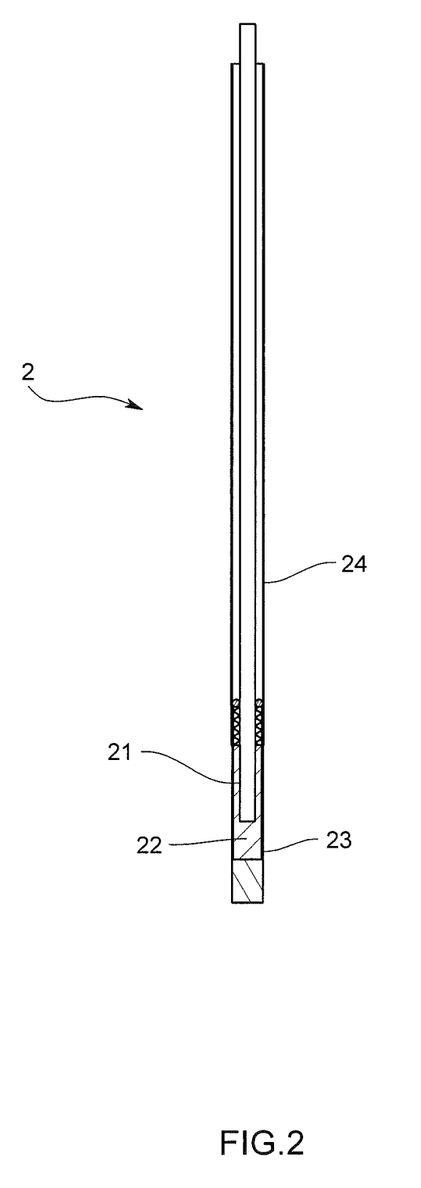
FIG. 2 is an overall schematic diagram schematically illustrating a configuration of a reference electrode of the same embodiment.
Figure 3:
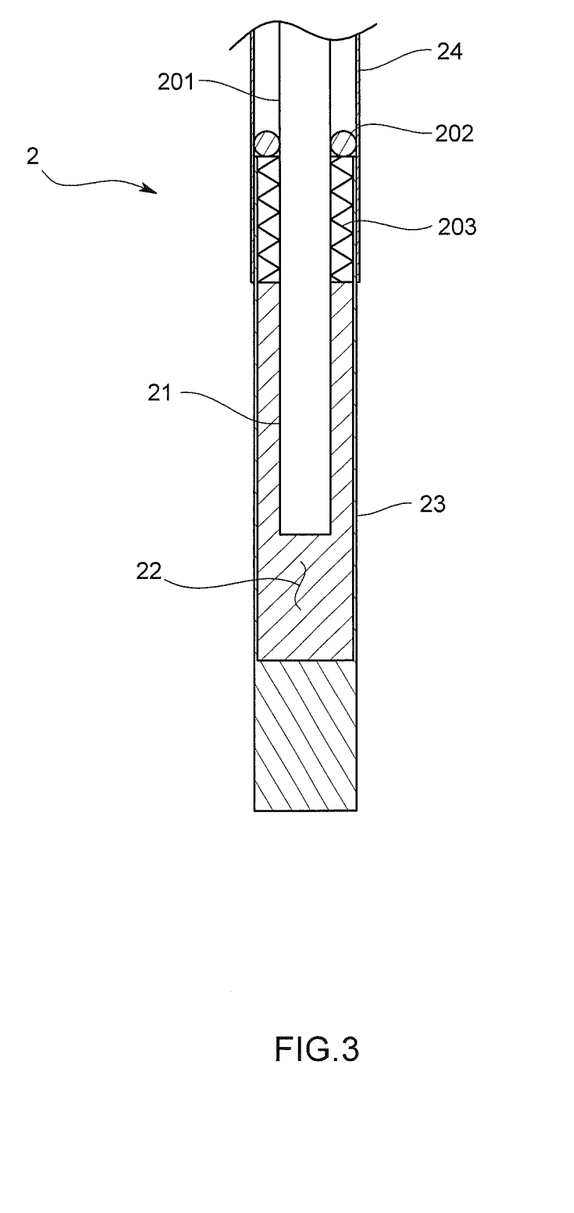
FIG. 3 is a partially enlarged cross-sectional view illustrating a fore end portion of the reference electrode of the same embodiment.

Also, the comparison electrode 2 is, as illustrated in FIGS. 2 and 3, provided with: an internal electrode 21 formed of a silver/silver chloride electrode; an internal electrolyte solution 22 that is in contact with the internal electrode 21; and a containing body that contains the internal electrolyte solution 22.

The internal electrode 21 is held by a holding tube 24 such that a fore end portion thereof is exposed outside. Also, a rear end portion of the internal electrode 21 is connected with the lead (not illustrated).

The internal electrolyte solution 22 is the highly concentrated (3.33 mol/L) KCl solution. Note that the internal electrolyte solution 22 is not limited to the KCl solution if it contains highly concentrated cations.

The containing body 23 is formed of a material that does not have anionic conductivity but has cationic conductivity and moisture permeability, specifically, formed of Flemion (Asahi Glass Co. Ltd., registered trademark) that is fluorine based resin. The containing body 23 of the present embodiment is formed of Flemion as a whole, and specifically, a bottom-equipped tubular body formed of Flemion.

The containing body 23 is adapted to be connected to a fore end portion of the holding tube 24 that holds the internal electrode 21, cover the fore end portion of the internal electrode 21 that is exposed outside from the holding tube 24, and bring the internal electrolyte solution 22 contained inside the containing body 23 into contact with the fore end portion of the internal electrode 21.

Next, a method for manufacturing the comparison electrode 2 configured as described is briefly described referring to FIG. 3.

For example, Flemion hollow fiber tube having a diameter of 1 mm is cut into a piece having a length of 10 mm, and one of end faces of the piece is blocked by a heat seal or the like to form a containing body formed product.

The containing body formed product fabricated as described above is immersed in a 3.33 mol/L KCL (AgCl room temperature saturated) solution for approximately 2 hours. At this time, a pH of the 3.33 mol/L KCL (AgCl room temperature saturated) solution is changed from approximately pH 6 to approximately pH 2.7 because a Flemion functional group $SO_3$—H is ion exchanged to $SO_3$—K.

The containing body formed product is picked up from the 3.33 mol/L KCl (AgCl room temperature saturated) solution, and after cleaning with pure water, dried by 60° C. a dryer or the like. This causes the containing body 23 to be formed.

On the other hand, for example, a silver wire 201 having a diameter of 0.6 mm is attached with mechanical seal such as an O-ring 202, then inserted into a polyimide tube serving as the holding tube 24, and fixed to the polyimide tube 24. At this time, a fore end portion of the silver wire 201 is in a state of being exposed from the polyimide tube 24 by a predetermined length.

The fore end portion of the silver wire 201 is immersed in a 3.33 mol/L KCl (AgCl room temperature saturated or 1 mol/L) solution up to approximately 4 mm in length and anodized for approximately 10 minutes with an applied voltage of approximately 1.3 to 1.5 V, and thereby the silver wire part is formed thereon with silver chloride on the basis of electrolysis, and after cleaning with pure water, kept in a dark room. This causes the silver/silver chloride electrode 21 to be formed.

A 3.33 mol/L KCl (AgCl room temperature saturated) solution is injected into the containing body 23 from the lower seal face up to approximately 3 mm in height.

Then, the silver wire 201, the O-ring 202, and the polyimide tube 24 are fixed; for example, a single component silicone RTV adhesive 203 is filled below the O-ring 202; and the containing body 23 is inserted into the polyimide tube 24 and fixed, and then dried and cured for 2 to 3 hours. The comparison electrode 2 fabricated as described above is kept with being immersed in a 3.33 mol/L KCl solution.

Next, an experimental example of the comparison electrode 2 configured as above is described in terms of respective performance parameters.

<Regarding Basic Performance>

Figure 4:
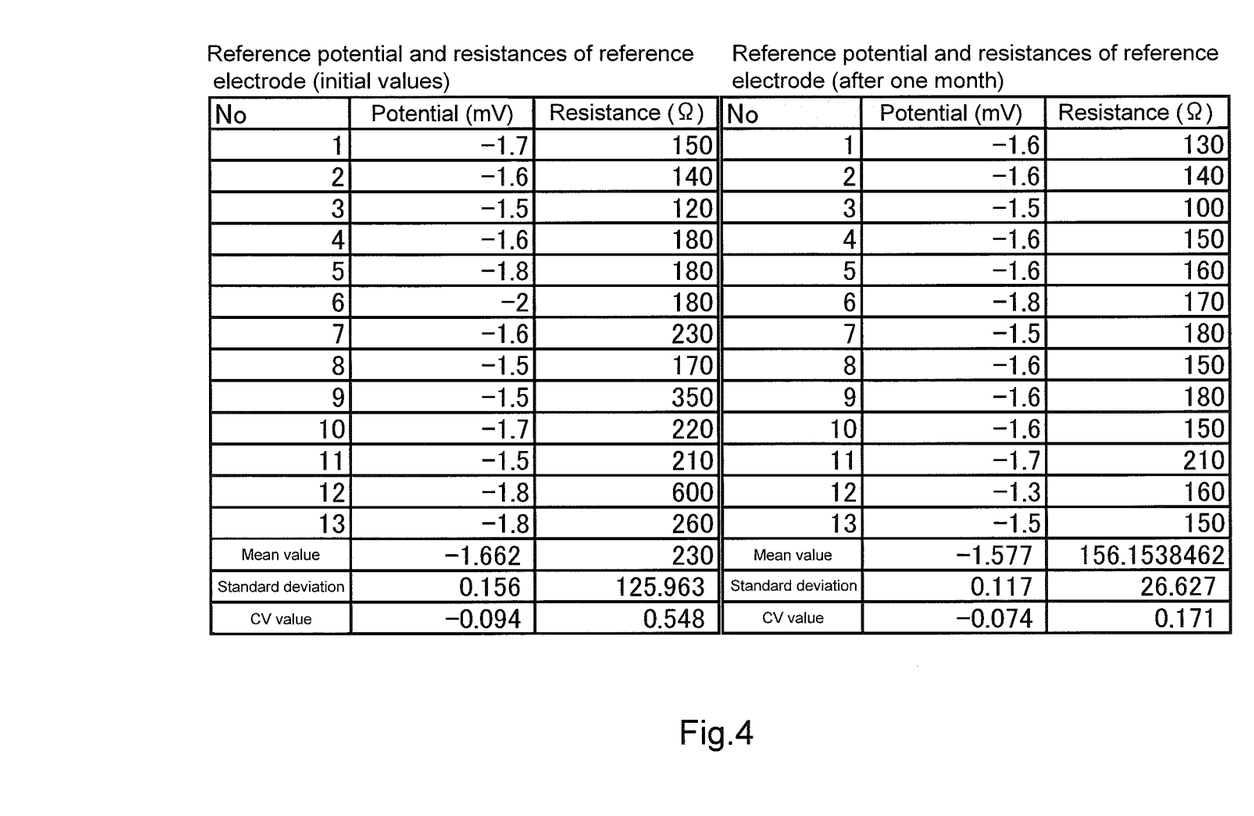
FIG. 4 is a diagram illustrating results of measuring an electrode potential of the reference electrode and a resistivity of the reference electrode in the same embodiment.

Results of measuring an electrode potential of the comparison electrode 2 (Vs, 3.33 mol/L KCl/AgCl/Ag (reference electrode), Ag/AgCl/3.33 mol/L KCl/3.33 mol/L KCl), and a resistance of the comparison electrode 2 (in 3.33 mol/L KCl) in the present embodiment at 25° C., and an electrode potential and a resistance after the comparison electrode 2 was left at room temperature for 1 month are illustrated in FIG. 4.

The comparison electrode 2 of the present embodiment exhibits a good result that a reference potential thereof is 2 mV or less with respect to a reference electrode, and a variation in reference potential is small. Further, an electrical resistance value of the containing body 23 is also 1 kΩ or less, and even when being added with a ceramic resistance value of the liquid communication part 103, can clear a predetermined standard value (e.g., less than 10 kΩ). Also, regarding behavior of the electrode potential over time, little variation is observed even after the comparison electrode 2 was left for one month with being immersed in a 3.33 mol/L KCl solution, and a good result is obtained. Note that the resistance tends to be slightly reduced as a whole, and a variation in resistance is also reduced, and therefore no performance problem occurs.

<Regarding Electrode Potential In KCl Solution>

Figure 5:
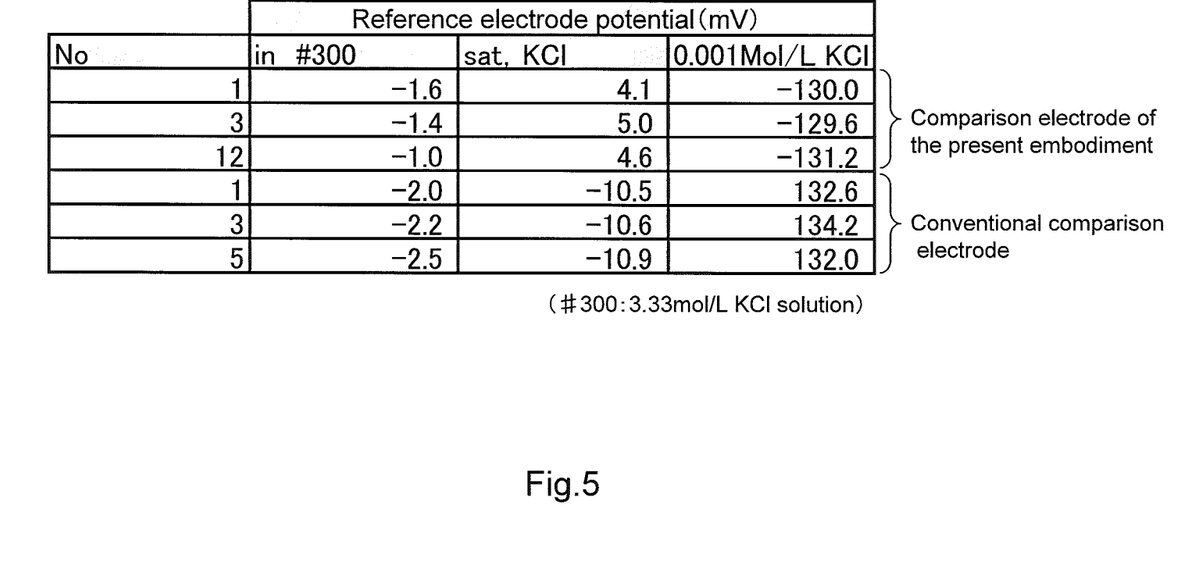
FIG. 5 is a diagram illustrating potential behavior of the reference electrode of the same embodiment and a conventional reference electrode with respect to a KCl concentration.

The containing body 23 made of Flemion has cation conductivity, and it is considered that if a cation concentration is different between the inside and outside of the containing body 23, a potential difference is generated between the inside and outside of the containing body 23 by a mechanism based on a diffusion potential. In the case of the comparison electrode 2 of the present embodiment, the immersion in the 3.33 mol/L KCl solution causes a $K^+$ ion concentration (activity) to be the same between the inside and the outside, and therefore a potential difference is not generated between the inside and outside of the containing body 23. However, it is determined that the potential difference is varied due to a variation in $K^+$ ion concentration of the internal liquid. In this case, the silver/silver chloride electrode 21 inside the containing body 23 is immersed in the 3.33 mol/L KCl (AgCl room temperature saturated) solution, and therefore exhibits a constant potential. Regarding the comparison electrode 2 of the present embodiment, the containing body 23 made of Flemion responds to cations, and therefore it is predicted that a potential is changed in a direction opposite to potential response behavior of a typical silver/silver chloride electrode, which is demonstrated by the present experiment (see FIG. 5).

<Regarding Anion Influence>

Figure 6:
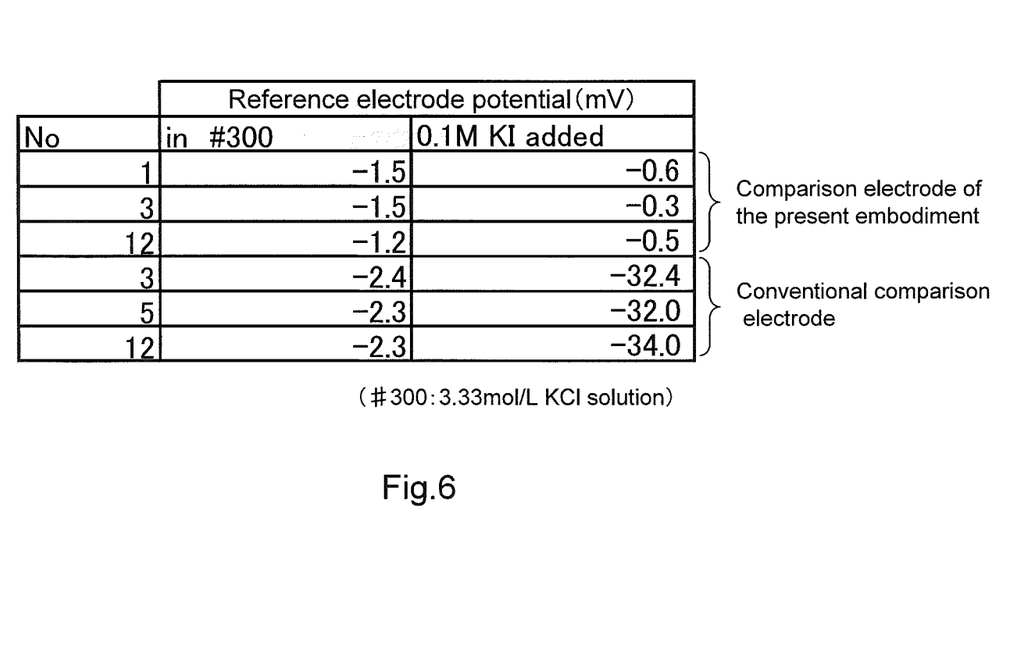
FIG. 6 is a diagram illustrating coexistence influence of halogen ions that form silver halogenide that is more poorly-soluble than silver chloride of the same embodiment.

A potassium iodide reagent was added to the internal liquid to measure the electrode potential of the comparison electrode 2 for the case of approximately 0.1 mol/L coexistence. A result of the measurement is illustrated in FIG. 6. The influence of iodide ions in a conventional comparison electrode is significant; however, in the comparison electrode 2 using the containing body 23 made of Flemion, the electrode potential is little influenced. This demonstrates that Flemion prevents anions from passing. The electrode potential is slightly varied toward a plus side, and this is highly likely to be due to an increase in $K^+$ ion concentration. Also, sulfide ions react with the silver/silver chloride electrode to form silver sulfide on a surface of the electrode, which is known as a coexisting material that largely influences the potential to prevent the measurement from being made.

<Regarding Influence of Ultraviolet Light>

It is known that the electrode potential of the silver/silver chloride electrode is largely influenced by ultraviolet light (maximum absorption wavelength 220 nm). To eliminate this, an effort to absorb ultraviolet light is made, typically, on the basis of a structure of the reference electrode, or by adding silver sulfide to silver chloride or other means. Regarding a degree of the influence on potential, a potential variation of a few 100 mV may occur under direct sunlight in a plus direction due to a silvering reaction of silver chloride. (An ultraviolet light amount under direct sunlight is 2 to 3.5 $mW/cm^2$, and that in a room is 0.1 $mW/cm^2$.)

Figure 7:
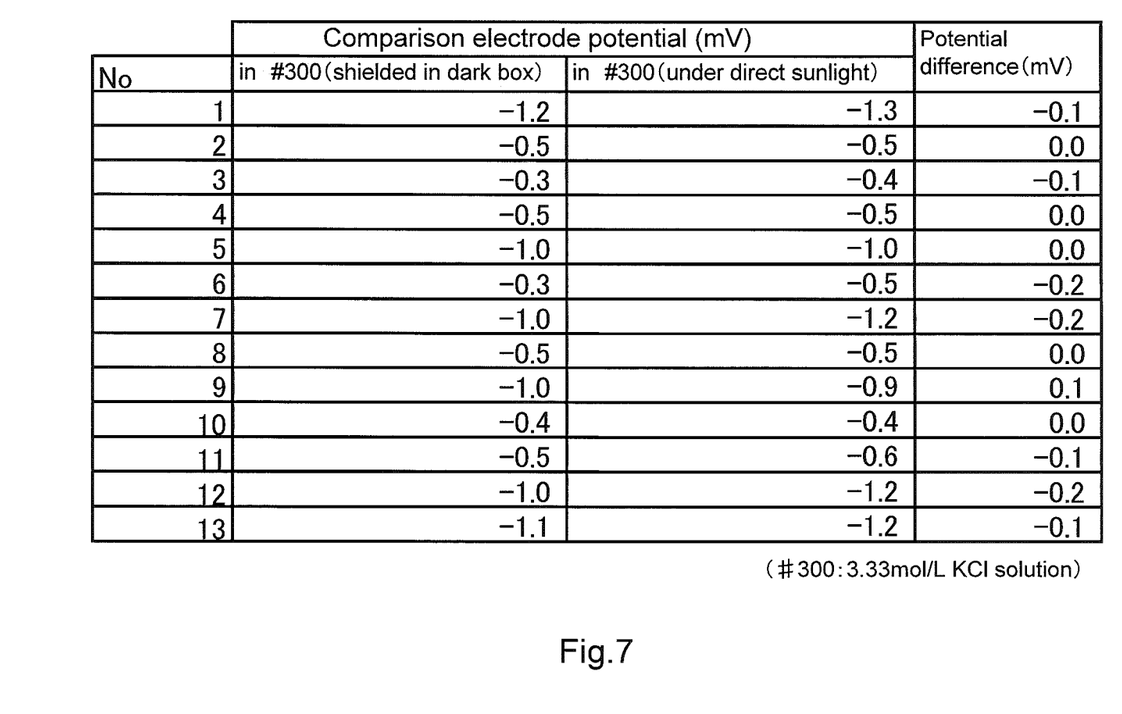
FIG. 7 is a diagram illustrating the influence on the reference electrode under direct sunlight.

On the basis of this, the influence on the comparison electrode under direct sunlight was examined. Measurement results for the case where the reference electrode 2 of the present embodiment was immersed in a 3.33 mol/L KCl solution and kept in a dark box and the case where the reference electrode 2 was placed on a rooftop under direct sunlight are illustrated in FIG. 7. As a result, the potential variation under direct sunlight is 0.5 mV or less, and the influence of ultraviolet light is not observed.

<Regarding Drying Influence>

The comparison electrode 2 of the present embodiment was left for three days in the 60° C. dryer to completely evaporate the internal electrolyte solution 22. The containing body 23 made of Flemion itself has no hole; however, if a vapor pressure is different between the inside and outside of the containing body 23, the containing body 23 fulfills a function of equilibrating the water vapor pressures with each other. Accordingly, in the case where humidity outside the containing body 23 is low, the internal electrolyte solution 22 is scattered toward the outside of the containing body 23 as moisture. On the other hand, in the case where the internal electrolyte solution 22 is dried, if being immersed in a 3.33 mol/L KCl solution, the containing body 23 is moistened, and internal crystallized and solidified KCl is dissolved and recovered into the 3.33 mol/L KCl solution.

Figure 8:
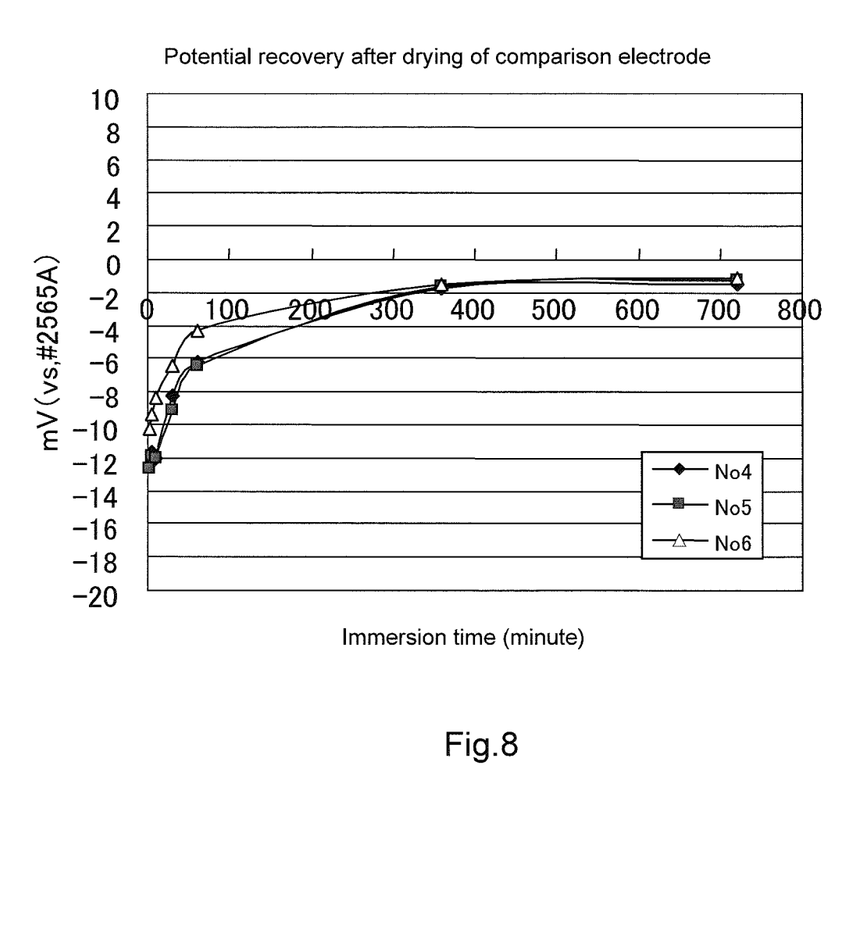
FIG. 8 is a diagram illustrating potential recovery after drying of the reference electrode.
Figure 9:
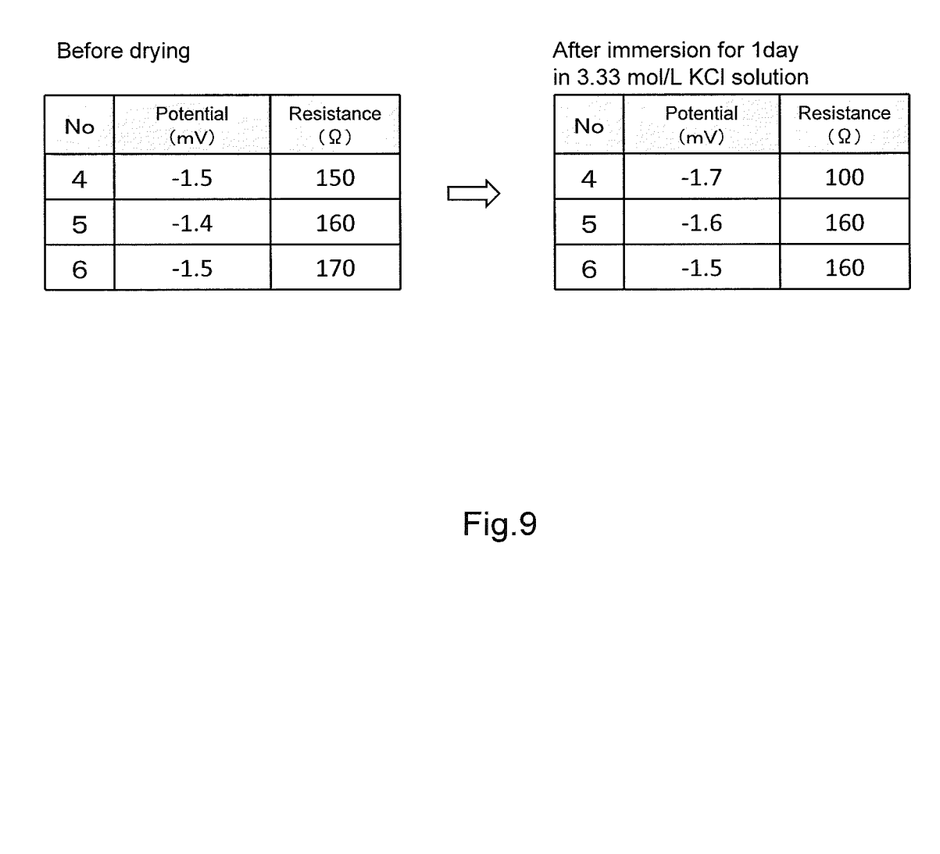
FIG. 9 is a diagram illustrating variations in an electrode potential and an internal resistance between before and after drying of the reference electrode.

When the inside of the containing body 23 is dried, KCl crystals exist in a solidified state. A recovery time for the case where this was immersed in a 3.33 mol/L KCl solution was measured. It turns out from FIGS. 8 and 9 that regarding recovery times of the potential and internal resistance after drying, for all of three types, after 30 minutes, the potential and internal resistance respectively fall within 10 mV and 1 kΩ. It also turns out from this that as compared with the conventional reference electrode having the silver ion trap structure, the recovery from drying is fast and therefore an improvement effect is significant. Furthermore, #2565A in the vertical axis of FIG. 8 is the comparison electrode made by HORIBA, Ltd.

<Effects of the Present Embodiment>

According to the comparison electrode 2 according to the present embodiment configured as described, the containing body 23 does not have anionic conductivity, and therefore chloride ions and silver chloride complexation anions produced by reaction with the chloride ions and silver ions eluted from the silver/silver chloride electrode 21 can be suppressed from being eluted. This enables a potential variation occurring due to production of a poorly-soluble silver compound on the surface of the comparison electrode to be suppressed. Besides, a potential variation occurring due to anions existing outside the containing body 23 can also be suppressed.

Also, it is considered that silver ions eluted from silver chloride are kept at a low concentration and do not diffuse into the internal electrolyte solution 22. This enables a silver/silver chloride electrode 21 having a relatively thin silver chloride layer to be employed, or a life of the silver/silver chloride electrode 21 to be extended.

Further, the containing body 23 does not have anionic conductivity but has cationic conductivity, and therefore a potential generated in the containing body 23 depends on a cation concentration of the internal electrolyte solution 22. In addition, the containing body 23 is formed of the material having moisture permeability, so that only by immersing the reference electrode 2 in a desired electrolyte solution, the internal electrolyte solution 22 can be recovered to an original state, and also a reference potential can be recovered. Note that the containing body 23 is only required to be immersed in a desired electrolyte solution, and therefore recovery work can be easily performed in a short time.

In addition, only by forming the containing body 23 with use of the material that does not have anionic conductivity but has cationic conductivity and moisture permeability, together with the above respective effects, production cost can be reduced on the basis of saving of an assembling man-hour.

<Other Variations>

Note that the present invention is not limited to the above-described embodiment.

For example, in the above-described embodiment, the containing body is made of Flemion; however, for the containing body, Nafion (registered trademark) may be used.

Also, the containing body in the above-described embodiment is formed of Flemion as a whole, and configured not to have anionic conductivity but have cationic conductivity and moisture permeability as a whole; however, the containing body may be configured such that a part of the containing body does not have anionic conductivity but has cationic conductivity and moisture permeability, and the other part does not have at least anionic conductivity.

Further, in the above-described embodiment, the composite electrode in which the reference electrode and the working electrode are integrated is described; however, the present invention may be configured to be the reference electrode as a single body.

Figure 10:
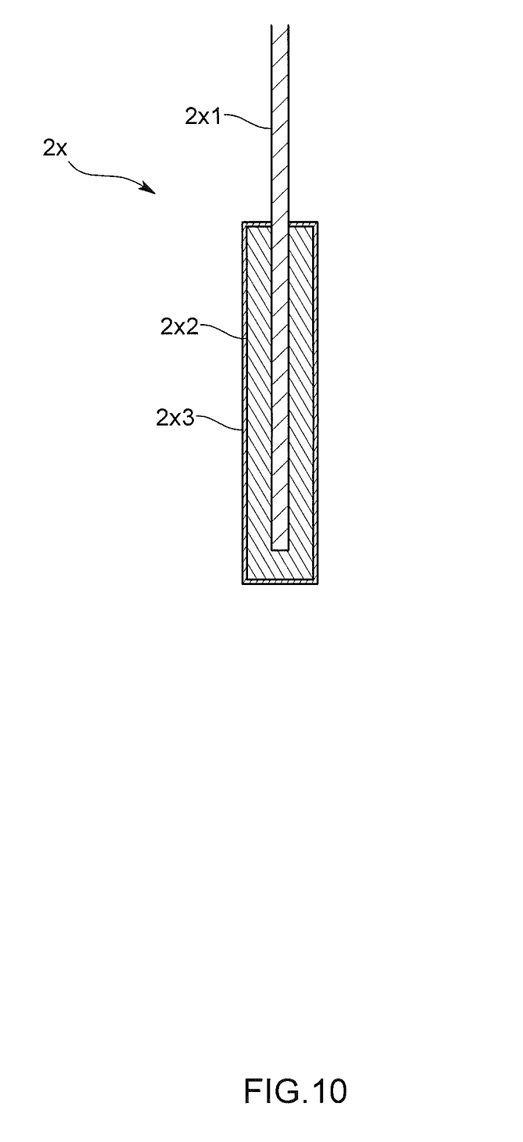
FIG. 10 is a cross-sectional view schematically illustrating a reference electrode according to a variation.

In addition, the above-described embodiment is configured to contain the internal electrolyte solution in the containing body; however, as illustrated in FIG. 10, even if a reference electrode 2x is one having: an electrode main body 2x1 comprising of silver; an eutectic salt layer 2x2 covering the electrode main body 2x1, comprising an eutectic mixture of silver chloride and a salt, and acting as an electrolyte; and an outside covering layer 2x3 comprising a material that does not have anionic conductivity but has cationic conductivity and moisture permeability, and covering the eutectic salt layer 2x2, the same effects as those of the reference electrode 2 of the above-described embodiment are produced. Note that an eutectic mixture of silver chloride and a salt can be obtained, for example, by adding a few % of KCl to silver chloride. As a method for covering the electrode main body 2x1 with the eutectic salt layer 2x2, for example, dip coating is possible. Also, by adding to the eutectic salt layer a material that absorbs ultraviolet light, for example, silver sulfide, the influence of ultraviolet light can be further reduced.

Besides, it should be appreciated that the present invention is not limited to any of the above-described embodiments, but can be variously modified without departing from the scope thereof.

Reference Signs List
100: Composite electrode
2: Reference electrode (comparison electrode)
3: Working electrode (pH electrode)
21: Internal electrode
22: Internal electrolyte solution
23: Containing body

The invention claimed is:

1. A reference electrode comprising:
an internal electrode formed of a silver/silver chloride electrode:
an internal electrolyte solution that is in contact with the internal electrode;
a containing body that contains the internal electrolyte solution; and
a holding tube that holds the internal electrode; wherein
the containing body is formed of a material that does not have anionic conductivity but has cationic conductivity and moisture permeability; and
the containing body is fixed to the holding tube by a mechanical seal and an adhesive.

2. The reference electrode according to claim 1, wherein
a whole of the containing body is formed of a material that does not have anionic conductivity but has cationic conductivity and moisture permeability.

3. A reference electrode having:
an electrode main body comprising silver;
an eutectic salt layer covering the electrode main body, comprising an eutectic mixture of silver chloride and a salt, the eutectic layer acting as an electrolyte;
an outside covering layer comprising a material having cationic conductivity and moisture permeability, and covering the eutectic salt layer; and
a holding tube that holds the internal electrode, wherein
the containing body is fixed to the holding tube by a mechanical seal and an adhesive.

* * * * *